US012415908B2

(12) United States Patent
Thiyagarajan et al.

(10) Patent No.: US 12,415,908 B2
(45) Date of Patent: Sep. 16, 2025

(54) POLYMER COMPOSITIONS AND PRODUCTS FORMED THEREWITH

(71) Applicant: Church & Dwight Co., Inc., Princeton, NJ (US)

(72) Inventors: Muthiah Thiyagarajan, Flemington, NJ (US); Rajesh Ranjan, Princeton, NJ (US); Carmen Guzman, Ewing, NJ (US); Jon Toliver, Franklin Park, NJ (US); Steven T. Adamy, Lawrenceville, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 18/762,307

(22) Filed: Jul. 2, 2024

(65) Prior Publication Data

US 2024/0352238 A1  Oct. 24, 2024

Related U.S. Application Data

(62) Division of application No. 17/125,369, filed on Dec. 17, 2020, now abandoned.

(60) Provisional application No. 63/018,311, filed on Apr. 30, 2020, provisional application No. 62/951,856, filed on Dec. 20, 2019.

(51) Int. Cl.
C08L 7/02 (2006.01)
A61F 6/04 (2006.01)
C08J 5/00 (2006.01)
C08J 5/02 (2006.01)
C08K 5/00 (2006.01)
C08K 5/40 (2006.01)
C08L 25/16 (2006.01)

(52) U.S. Cl.
CPC ............... C08L 7/02 (2013.01); A61F 6/04 (2013.01); C08J 5/02 (2013.01); C08K 5/005 (2013.01); C08K 5/40 (2013.01); C08L 25/16 (2013.01); C08J 2307/02 (2013.01); C08J 2309/08 (2013.01); C08J 2325/16 (2013.01)

(58) Field of Classification Search
CPC ..................... C08J 5/005; A61F 6/04
See application file for complete search history.

(56) References Cited

U.S. PATENT DOCUMENTS

| 3,215,649 | A | 11/1965 | Preiss et al. |
|---|---|---|---|
| 3,238,173 | A | 3/1966 | Bailey et al. |
| 3,261,792 | A | 7/1966 | Halper et al. |
| 3,360,599 | A | 12/1967 | Nyberg et al. |
| 3,988,275 | A | 10/1976 | Satake et al. |
| 5,082,732 | A | 1/1992 | Ueda et al. |
| 5,444,121 | A | 8/1995 | Grennes et al. |
| 5,500,469 | A | 3/1996 | Johnsen et al. |
| 5,513,654 | A | 5/1996 | Delson |
| 5,728,340 | A | 3/1998 | Dreibelbis et al. |
| 5,744,540 | A | 4/1998 | Baumstark et al. |
| 5,851,683 | A | 12/1998 | Plamthottam et al. |
| 6,021,524 | A | 2/2000 | Wu et al. |
| 6,121,366 | A | 9/2000 | Sharma |
| 6,492,446 | B1 | 12/2002 | Kajiwara et al. |
| 6,559,255 | B2 | 5/2003 | Klaerner et al. |
| 6,579,937 | B1 | 6/2003 | Guentherberg et al. |
| 6,579,940 | B1 | 6/2003 | Dove |
| 6,828,387 | B2 * | 12/2004 | Wang ............... C08L 9/10 524/565 |
| 6,833,276 | B2 | 12/2004 | Klaerner et al. |
| 6,867,254 | B2 | 3/2005 | Wiercinski et al. |
| 6,914,091 | B2 | 7/2005 | Donald et al. |
| 6,920,643 | B2 | 7/2005 | McGlothlin et al. |
| 6,998,158 | B2 | 2/2006 | Hoerner et al. |
| 7,041,367 | B2 | 5/2006 | Janssen et al. |
| 7,048,979 | B2 | 5/2006 | Wright et al. |
| 7,179,849 | B2 | 2/2007 | Terry |
| 7,265,192 | B2 | 9/2007 | Soerens |
| 7,329,442 | B2 | 2/2008 | Modha et al. |
| 7,344,568 | B2 | 3/2008 | Chen |
| 7,374,711 | B2 | 5/2008 | McGlothlin et al. |
| 7,531,594 | B2 | 5/2009 | Lin et al. |
| 7,582,702 | B2 | 9/2009 | Wright et al. |

(Continued)

FOREIGN PATENT DOCUMENTS

| CA | 2716805 C | 11/2017 |
|---|---|---|
| CN | 103921352 | 7/2014 |

(Continued)

OTHER PUBLICATIONS

Hanus, et al., "Electrolyte-Induced Aggregation of Acrylic Latex. 1. Dilute Particle Concentrations", Center for Molecular and Engineering Thermodynamics, Department of Chemical Engineering, University of Delaware, Newark, DE, Publication: Langmuir 2001, vol. 17, No. 11, pp. 3136-3147. US.

Mayer, et al., "Emulsion Polymerization of Styrene with Disproportionated Rosin Acid Soap as Emulsifier", Journal of pplied Polymer Science, vol. 59, 1047 (1996) US.

Vera, et al., "Colloidal Stability of a Pharmaceutical Latex: Experimental Determinations and Theoretical Predictions", Ournal of Colloid and Interface Science, vol. 117, pp. 553-560 (1996), Article No. 0069. ES.

Primary Examiner — Vickey Nerangis
(74) Attorney, Agent, or Firm — Church & Dwight Co., Inc.

(57) ABSTRACT

The present disclosure provides compositions and products formed therefrom. In particular, the disclosure provides elastomeric latex articles, such as gloves and condoms, that can be prepared utilizing a styrene-polyisoprene-styrene (SIS) latex. The elastomeric articles can exhibit desired tensile properties while being substantially or completely free of undesired components, such as sulfur and zinc oxide, which can be allergens. The disclosure further provides methods of preparing elastomeric latex articles.

16 Claims, 1 Drawing Sheet

(56) References Cited

U.S. PATENT DOCUMENTS

| | | |
|---|---|---|
| 7,585,916 B2 | 9/2009 | Wright et al. |
| 7,662,890 B2 | 2/2010 | Aida et al. |
| 7,700,705 B2 | 4/2010 | Jole |
| 8,003,209 B2 | 8/2011 | Flood et al. |
| 8,087,412 B2* | 1/2012 | Lucas .................. C08L 23/20 |
| | | 128/842 |
| 8,104,097 B2 | 1/2012 | Hamann |
| 8,117,672 B2 | 2/2012 | Lipinski |
| 8,273,810 B2 | 9/2012 | Wang et al. |
| 8,399,105 B2 | 3/2013 | Butz et al. |
| 8,431,667 B2 | 4/2013 | Cornish et al. |
| 8,436,087 B2 | 5/2013 | Foo |
| 8,492,480 B2 | 7/2013 | Takeshi et al. |
| 8,530,016 B2 | 9/2013 | Wang et al. |
| 8,633,268 B2 | 1/2014 | Lawson et al. |
| 8,651,110 B2 | 2/2014 | Hui |
| 8,673,172 B2 | 3/2014 | Jole |
| 8,680,191 B2 | 3/2014 | Foo |
| 8,829,083 B2 | 9/2014 | Lundgard et al. |
| 8,835,014 B2 | 9/2014 | Wang et al. |
| 8,856,506 B2 | 10/2014 | Weber et al. |
| 9,000,090 B2 | 4/2015 | Attrill et al. |
| 9,074,027 B2 | 7/2015 | Lucas et al. |
| 9,074,029 B2 | 7/2015 | Lucas et al. |
| 9,085,100 B2 | 7/2015 | Foo |
| 9,296,850 B2 | 3/2016 | Feher et al. |
| 9,321,932 B2 | 4/2016 | De Jong |
| 9,527,226 B2 | 12/2016 | Foo |
| 9,694,519 B2 | 7/2017 | Foo |
| 9,758,648 B2 | 9/2017 | Van der Waal et al. |
| 9,932,463 B2 | 4/2018 | Van der Waal et al. |
| 9,951,160 B2 | 4/2018 | Huizen et al. |
| 9,994,694 B2 | 6/2018 | De Jong et al. |
| 10,047,212 B2 | 8/2018 | Van der Waal et al. |
| 10,066,100 B2 | 9/2018 | Greger |
| 10,125,239 B2 | 11/2018 | Chen et al. |
| 10,214,621 B2 | 2/2019 | Potter et al. |
| 10,385,156 B2 | 8/2019 | Zhou et al. |
| 10,456,290 B2 | 10/2019 | Oleson et al. |
| 10,517,338 B2 | 12/2019 | Chen et al. |
| 10,538,609 B2 | 1/2020 | Lucas et al. |
| 11,958,969 B2 | 4/2024 | Kodemura |
| 2002/0061981 A1 | 5/2002 | Donald et al. |
| 2002/0061982 A1 | 5/2002 | Donald et al. |
| 2003/0161975 A1 | 8/2003 | Lucas et al. |
| 2003/0175458 A1 | 9/2003 | Jain et al. |
| 2004/0071909 A1 | 4/2004 | McGlothlin et al. |
| 2004/0105943 A1 | 6/2004 | Hoerner et al. |
| 2004/0147661 A1 | 7/2004 | Yaakub et al. |
| 2006/0173137 A1 | 8/2006 | McGlothlin et al. |
| 2009/0272384 A1 | 11/2009 | Lucas |
| 2010/0204397 A1 | 8/2010 | Kobayashi et al. |
| 2011/0178234 A1 | 7/2011 | Wang et al. |
| 2014/0142211 A1 | 5/2014 | Stoever et al. |
| 2014/0171540 A1 | 6/2014 | De Jong |
| 2015/0087761 A1 | 3/2015 | Satoh et al. |
| 2015/0128329 A1 | 5/2015 | Amarasekera et al. |
| 2015/0272245 A1 | 10/2015 | Khor et al. |
| 2016/0040033 A1 | 2/2016 | Harrison et al. |
| 2016/0108154 A1* | 4/2016 | Krutzer ................ C08K 5/0025 |
| | | 526/192 |
| 2016/0159992 A1 | 6/2016 | Foo et al. |
| 2017/0107403 A1 | 4/2017 | Woo et al. |
| 2017/0274566 A1 | 9/2017 | Foo |
| 2017/0333602 A1 | 11/2017 | Amiralian et al. |
| 2018/0193237 A1 | 7/2018 | Foo et al. |
| 2018/0346754 A1 | 12/2018 | MacDonald |
| 2019/0010271 A1 | 1/2019 | Kodemura et al. |
| 2019/0023854 A1 | 1/2019 | Ishii et al. |
| 2019/0031788 A1 | 1/2019 | Kodemura et al. |
| 2019/0031861 A1 | 1/2019 | Satoh et al. |
| 2019/0031865 A1 | 1/2019 | Ishii et al. |
| 2019/0055367 A1 | 2/2019 | Shiba et al. |
| 2019/0177496 A1 | 6/2019 | Chen et al. |
| 2019/0218375 A1 | 7/2019 | Lucas et al. |
| 2019/0270863 A1 | 9/2019 | Leng et al. |
| 2019/0292331 A1 | 9/2019 | Wang et al. |
| 2019/0292361 A1 | 9/2019 | Flood et al. |
| 2019/0300685 A1 | 10/2019 | Ishiba et al. |
| 2019/0321214 A1 | 10/2019 | Wang |
| 2019/0367687 A1 | 12/2019 | Kodemura et al. |
| 2020/0010651 A1 | 1/2020 | Aihara et al. |
| 2020/0062873 A1 | 2/2020 | Kodemura et al. |
| 2020/0199311 A1 | 6/2020 | Foo et al. |
| 2021/0189106 A1 | 6/2021 | Thiyagarajan et al. |

FOREIGN PATENT DOCUMENTS

| | | |
|---|---|---|
| CN | 103921382 A | 7/2014 |
| EP | 2799483 B1 | 8/2017 |
| EP | 3155019 A4 | 1/2018 |
| GB | 1028357 | 5/1966 |
| GB | 2436566 | 10/2007 |
| JP | 2016141691 | 8/2016 |
| NL | 2011591 | 4/2015 |
| WO | WO 95/00586 A1 | 1/1995 |
| WO | WO 2003/022891 | 3/2003 |
| WO | WO 2006/027164 | 3/2006 |
| WO | WO 2011/157033 | 12/2011 |
| WO | WO 2016/061043 | 4/2016 |
| WO | WO 2018117812 | 6/2018 |
| WO | WO 2018/194904 | 10/2018 |
| WO | WO 2018/207683 | 11/2018 |
| WO | WO 2018/224881 | 12/2018 |
| WO | WO 2019/039523 | 2/2019 |
| WO | WO 2019/073890 | 4/2019 |
| WO | 2019183302 A1 | 9/2019 |
| WO | WO 2019/171981 | 9/2019 |
| WO | WO 2019/197520 | 10/2019 |
| WO | WO 2019/216241 | 11/2019 |
| WO | WO 2019/218088 | 11/2019 |
| WO | WO 2019/003744 A1 | 4/2020 |
| WO | WO 2020/131267 A1 | 6/2020 |
| WO | WO 2021/124215 A2 | 6/2021 |
| WO | WO 2020/045102 A1 | 8/2021 |

* cited by examiner

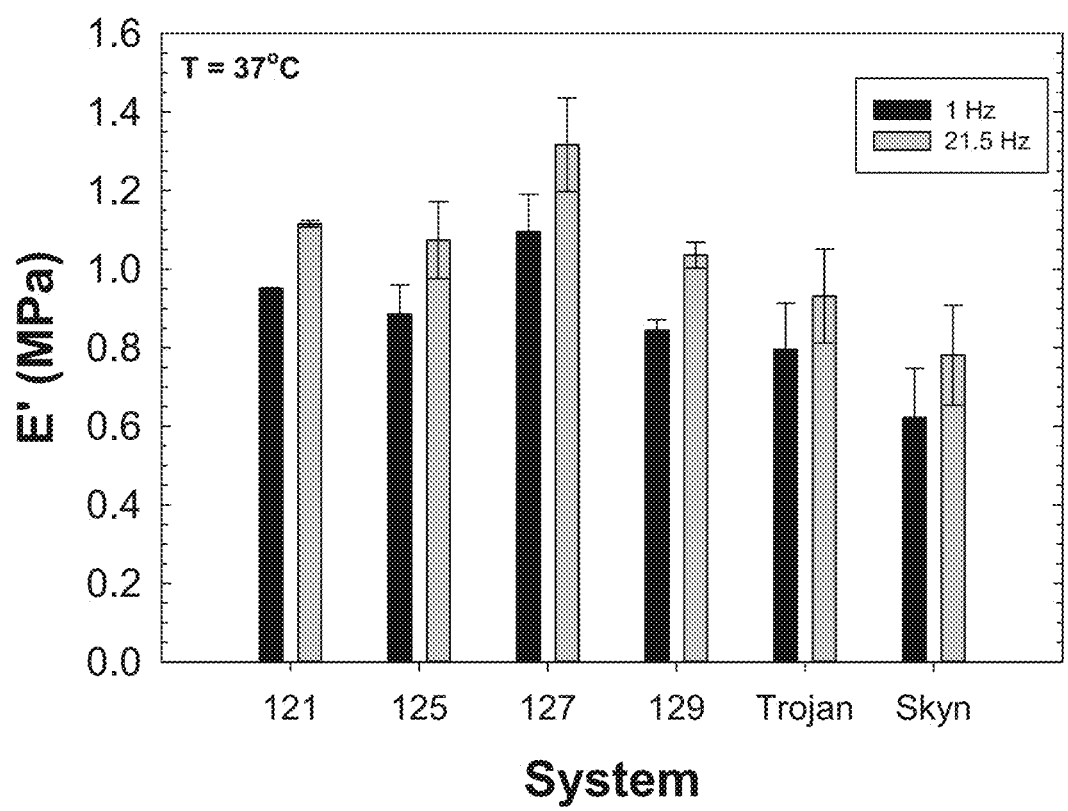

POLYMER COMPOSITIONS AND PRODUCTS FORMED THEREWITH

CROSS-REFERENCE TO RELATED APPLICATIONS

The present application is a Divisional of U.S. patent application Ser. No. 17/125,369, filed Dec. 17, 2020, which claims priority to U.S. Provisional Pat. App. No. 62/951,856, filed Dec. 20, 2019, and U.S. Provisional Pat. App. No. 63/018,311, filed Apr. 30, 2020, the disclosures of which are incorporated herein by reference in their entireties.

FIELD OF THE DISCLOSURE

The present disclosure relates to polymer compositions and products that are formed from the polymer compositions, such as elastomeric articles (e.g., thin-walled products, such as gloves and condoms). The present disclosure further relates to methods of making such products.

BACKGROUND

Natural rubber, which is comprised primarily of cis-1,4-polyisoprene, is well known for use in making thin-film, elastomeric articles, such as surgical gloves, balloons, condoms, and the like. However, articles formed from natural rubber latex are associated with a number of health problems, such as allergic reactions. As a result, some have turned to synthetic polyisoprene as a replacement for natural rubber in such articles. Because of the desire to achieve articles with excellent tensile properties, however, polyisoprene articles have typically been vulcanized similarly to natural rubbers using sulfur-based curing agents and zinc oxide cure activators. While avoiding some of the problems associated with the use of natural rubber, the requirement for using sulfur and zinc oxide can nevertheless also present health concerns arising from allergic reactions as well. Accordingly, there remains a need in the field for compositions and articles formed therefrom that are thin-film forming materials and that can provide articles with the desired tensile properties without the health concerns noted above.

SUMMARY OF THE DISCLOSURE

The present disclosure provides compositions of polymeric materials and products made therefrom. The products may include any material that is useful when provided in the form of a thin film that is elastomeric and exhibits substantially high tensile strength, such as gloves, condoms, and similar articles. The present disclosure further provides methods of preparing polymeric compositions and products.

In one or more embodiments, the present disclosure provides elastomeric articles comprising one or more layers of a compounded polystyrene-polyisoprene-polystyrene (SIS) latex composition. More particularly, the elastomeric articles can be configured to exhibit specific properties. For example, at a thickness of about 0.1 mm or less, the elastomeric articles can be configured to exhibit a tensile strength of about 20 MPa or greater when measured in accordance with ASTM D412 and exhibit a tensile modulus at 500% elongation of less than 2.25 MPa when measured in accordance with ASTM D412. The elastomeric articles may be further defined in relation to one or more of the following statements, which can be combined in any order or number.

The SIS latex composition can be substantially free of one or more of the following: elemental sulfur or free sulfur; zinc oxide; and diphenyl guanidine.

The elastomeric article can exhibit an elongation at break of about 1000% or greater.

The elastomeric article can exhibit a tear strength of at least 2 N/mm when measured in accordance with ASTM D624-00.

The elastomeric article can exhibit a Young's modulus (E') that is less than 1 MPa at a frequency of 1 Hz and that is greater than 1 MPa at a frequency of 21.5 Hz.

The SIS latex composition further can comprise a dithiocarbamate accelerator.

The SIS latex composition further can comprise a thiuram accelerator.

The SIS latex composition further can comprise one or more of a surfactant, an antioxidant, a viscosity modifier, a filler, and a smoothing agent.

The SIS latex composition can comprise a viscosity modifier including at least a hydrophobically modified alkali soluble emulsion.

The elastomeric article can be a condom.

In some embodiments, the present disclosure can provide elastomeric articles formed from composition comprising specific combinations of materials. In particular, such elastomeric articles may be formed from compositions comprising: polystyrene-polyisoprene-polystyrene (SIS) latex; an amphoteric surfactant; at least one sulfur donor; and at least one dithiocarbamate accelerator. The elastomeric articles may be further defined in relation to one or more of the following statements, which can be combined in any order or number.

The composition can comprise the amphoteric surfactant in an amount of 0.01 to about 2.0 phr.

The composition can comprise the dithiocarbamates accelerator in an amount of about 0.1 to about 2.0 phr.

The composition can comprise the at least one sulfur donor in an amount of about 0.1 to about 2.0 phr.

The at least one sulfur donor can comprise a thiuram compound.

The composition further can comprise one or more of an antioxidant, a viscosity modifier, a filler, and a smoothing agent.

The elastomeric article at a thickness of about 0.1 mm or less can exhibit a tensile strength of about 20 MPa or greater when measured in accordance with ASTM D412 and can exhibit a tensile modulus at 500% elongation of less than 2.25 MPa when measured in accordance with ASTM D412.

The composition can be substantially free of one or more of the following: elemental sulfur or free sulfur; zinc oxide; and diphenyl guanidine In further embodiments, the present disclosure can provide methods for preparing an elastomeric article. In particular, the methods can comprise forming a film on a former using two separate formulations having different overall compositions, each of the two separate formulations comprising a polystyrene-polyisoprene-polystyrene (SIS) polymer. Such methods may be further defined in relation to one or more of the following statements, which can be combined in any order or number.

One of the two separate formulations can include one or more cure accelerators and one or more surfactants, and wherein another of the two separate formulations expressly excludes any cure accelerators or cure agents.

The method can comprise sequential dipping of the former into separate containers that separately contain the two separate formulations to form the film on the former.

The method further can comprise separating the sequential dipping of the former into the separate containers with a drying period that is carried out at a temperature of about 50° C. or greater for a time of about 1 minute or greater.

The method further can comprise curing the film formed by the sequential dipping of the former into the separate container, and the curing is carried out at a temperature of about 100° C. or greater for a time of about 5 minutes or greater.

In other embodiments, the present disclosure can provide methods for preparing an elastomeric article that do not necessarily require the use of multiple, different formulations. For example, such methods can comprise: preparing a compounded latex composition include a polystyrene-polyisoprene-polystyrene (SIS) latex, at least one sulfur donor, and at least one dithiocarbamate accelerator; prevulcanizing the compounded latex composition to form a prevulcanized compounded latex composition; dipping a former into the prevulcanized compounded latex composition to form at least one layer of the prevulcanized compounded latex composition thereon; and curing the at least one layer of the prevulcanized compounded latex composition on the former to provide the elastomeric article. Such methods may be further defined in relation to one or more of the following statements, which can be combined in any order or number.

The at least one sulfur donor can be a thiuram compound.

The at least one sulfur donor can include one or both of dipentamethylenethiuram tetrasulfide (DPTT) and dipentamethylenethiuram hexasulfide (DPTTH).

The compounded latex composition further can include at least one amphoteric surfactant.

The compounded latex composition further can include at least one antioxidant.

The method further can comprise prevulcanizing the compounded latex composition in a temperature range of about 25° C. to about 40° C. for a time of about 12 hours to about 48 hours.

The method further can comprise prevulcanizing the compounded latex composition until achieving a relaxed modulus of about 0.50 to about 0.61.

In still further embodiments, the present disclosure can relate to elastomeric articles that are prepared according to one or more of the methods described herein. In particular, the elastomeric article can be a condom. Moreover, the elastomeric article at a thickness of about 0.1 mm or less can exhibit one or both of a tensile strength of about 20 MPa or greater when measured in accordance with ASTM D412 and a tensile modulus at 500% elongation of less than 2.25 MPa when measured in accordance with ASTM D412.

BRIEF DESCRIPTION OF THE DRAWING

FIG. 1 is a graph showing Young's modulus (E') values for various elastomeric articles according to the present disclosure compared with known elastomeric articles.

DETAILED DESCRIPTION OF THE DISCLOSURE

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to polymer compositions, more specifically to synthetic latex compositions. The present disclosure further relates to products that are formed from the polymer compositions as well as methods of making such products. The polymer compositions are particularly useful in preparing articles that can exhibit excellent physical properties even in the absence of additives that are often found in convention elastomeric articles and that can be a potential source of allergens.

The compositions provided herein and the products that may be prepared therefrom can comprise primarily a styrene-modified polyisoprene rubber material. More particularly, a poly(styrene-isoprene-styrene) material may be used, which may also be referred to as a polystyrene-polyisoprene-polystyrene material or "SIS" material or SIS polymer. The SIS polymer in particular can be a block copolymer that can be provided in the form of an aqueous latex dispersion. For example, suitable SIS polymer is available from Kraton Polymers under the name 2GL in their Cariflex® polymer line. The SIS latex material used according to the present disclosure can have a solids content of about 40% to about 65%, such as about 45% to about 65% or about 45% to about 55%.

In some embodiments, the SIS polymer may be characterized in relation to the relative content of the styrene and isoprene monomer blocks. Test data confirmed that all types of SIS polymers will not necessarily achieve an elastomeric article meeting the performance requirements described herein. In particular, both of tensile strength and modulus tend to increase with an increase in styrene content in the SIS polymer, but the relative increases are not of the same magnitude. Thus, styrene content in a SIS polymer can have a significant impact on the usefulness of an article prepared with the SIS polymer, particular in instances, as described herein, where high tensile strength but low modulus are preferred. Preferably, a SIS polymer useful according to the present disclosure includes a styrene content that is within a range that is defined by the weight percentage of styrene in the polymer block polymer backbone structure as compared to the overall molecular weight of the polymer (e.g., a wt/wt % of styrene in the overall polymer). For example, in some embodiments, the SIS polymer used according to the present disclosure can comprise at least 12%, at least 12.6%, or at least 13% styrene based on the total weight of the SIS polymer. The term "at least" in this instance can be defined, in some embodiments, as having a maximum of about 25%. Thus, in some embodiments, a SIS polymer as used herein can have a styrene content of about 12% to about 25%, about 12.6% to about 18%, about 13% to about 16%, or about 13.5% to about 15% by weight, based on the total weight of the SIS polymer. As further discussed herein, a preferred SIS polymer may be defined by a plurality of separate characteristics that make the polymer particular useful in forming an elastomeric article with desired properties. It has been found herein that the styrene content can affect one or more of the further properties that are desired. For example, it can be preferable for relaxed modulus of the SIS polymer to be within a defined range, and use of a SIS polymer with a styrene content outside of a preferred range can be detrimental to the desired relaxed modules property of the elastomeric article formed with the SIS polymer. In particular, it can be beneficial for the styrene content of the SIS polymer to be within the range of about 12% to about 16%, and more preferably about 13% to about 16%. Thus, while the present disclosure contemplates the ability to form an elastomeric article utilizing a SIS polymer with a styrene content that is greater than 16% wt/wt, such as a higher range noted above, the specific range of about 12% to about 16% can be particularly beneficial for enabling the elastomeric article to exhibit one or more properties as described herein, and specifically tensile strength and relaxed modulus.

SIS latex compositions according to the present disclosure can be used in forming elastomeric articles that exhibit desirable strength and softness properties, provide thermoplastic-like behavior, and also can be prepared without typical curing agents and/or curing accelerators that may be allergen sources. A SIS latex composition may comprise substantially only the SIS latex material in an aqueous dispersion. In some embodiments, the SIS latex compositions may include one or more additives that are useful to provide further, desired properties to the articles prepared therefrom, and such additives are further described below. Such compositions may be referred to herein as a compounded SIS latex, and it is understood that the term "compounded SIS latex composition" can specifically reference compositions including the SIS latex dispersion combined with one or more further components. Moreover, if desired, further polymer materials may be combined with the SIS polymer to provide combination polymer compositions. For example, in some embodiments, it may be useful to combine a content of a natural rubber latex ("NRL") with a content of a SIS polymer to provide a polymer composition for use in forming at least a part of an elastomeric article. For example, in embodiments further described herein wherein a binary process is utilized, it may be useful to utilize a combination of SIS latex and natural rubber latex as one dipping or coating formulation. In some embodiments, a ratio of NRL to SIS latex can be about 0.01 to about 0.1, about 0.02 to about 0.08, or about 0.03 to about 0.07, based on the weight of NRL and the weight of SIS polymer used in the composition (i.e., a wt/wt ratio). The foregoing ratios may apply to a single latex composition from which one or more layers may be formed through dipping. Alternatively, the foregoing ratios may apply to an end product (i.e., an elastomeric article) where at least NRL is used in one or more layers forming the product and at least SIS is used in one or more layers forming the product.

A wide variety of elastomeric articles may be prepared using compounded SIS latex compositions according to the preset disclosure. The compositions may be utilized to form films comprising one or a plurality of layers, and the films may particularly be provided in specific forms to provide elastomeric articles having desired end uses. For example, the compositions may be utilized in preparing elastomeric gloves, condoms, protective films for medical instruments, and other like uses where a substantially thin, elastomeric film is desirable.

In one or more embodiments, the present disclosure thus can provide elastomeric articles comprising one or more layers of a compounded SIS latex composition. The one or more layers may be in the form of a single film, a plurality of films that are independent but at least partially adhered or otherwise bonded together, or a plurality of films that are at least partially blended together. In some embodiments, multiple films may be combined in such a manner that the films blend together (at least partially) at surfaces thereof such that a unitary, single film or layer results (i.e., a plurality of films or layers are sufficiently intimately blended together at the film or layer surfaces such that the films or layers are substantially inseparable). Such instances are readily envisioned in light of the processing discussion provided further herein in relation to dipping or otherwise forming a plurality of films or layers on a former or similar structure so that sequentially applied films or layers become blended or bonded together to form substantially a single film or layer.

The polymer compositions and/or articles formed therefrom may be defined in one or more embodiments in relation to the absence of certain components that are commonly present in similar articles and compositions but may be undesirable. For example, in some embodiments, the SIS latex composition and/or an elastomeric article formed therewith may be substantially free or completely free of any free sulfur or elemental sulfur. As further discussed herein, certain composition components may be sulfur-containing materials (e.g., "sulfur donors"), but the sulfur therein is bound in a compound form. Conventional vulcanization reactions, however, typically utilize soluble sulfur (e.g., $S_8$ rings) that are easily solubilized to provide free, elemental sulfur in the mixture to participate in crosslinking. The present compositions may be substantially free or completely free of such free sulfur or elemental sulfur. In some embodiments, the SIS latex composition and/or an elastomeric article formed therewith may be substantially free or completely free of any zinc oxide. While zinc oxide is commonly used as a cure activator in known elastomeric articles, the presently disclosed compositions advantageously can be used to form elastomeric articles without the need for utilizing such cure activator. Similarly, the SIS latex composition and/or an elastomeric article formed therewith may be substantially free or completely free of any diphenyl guanidine cure accelerator, which also is commonly used in known elastomeric articles. As used above, "substantially" free can indicate that no more than a trace amount of the referenced material or compound is present, such as less than 0.1%, less than 0.05%, or less than 0.01% by weight.

A SIS latex composition useful according to the present disclosure may comprise substantially only the SIS latex dispersion. For example, as discussed further below, elastomeric articles may be prepared utilizing a plurality of different formulations for a plurality of individual dipping or other coating steps. A suitable formulation for use in forming at least one film or layer in making an elastomeric article thus may consist essentially or consist of a SIS latex dispersion or an aqueous SIS polymer.

In some embodiments, a compounded SIS latex composition may include one or more further components in addition to the SIS latex dispersion. The combination of the SIS latex dispersion and the one or more further components can be referred to as a compounded latex composition.

In one or more embodiments, one or more cure accelerators may be included in the SIS latex composition. Suitable cure accelerators can include, for example, one or more dithiocarbamates. Non-limiting examples of suitable dithiocarbamates can include zinc dibutyldithiocarbamate (ZDBC), zinc diethydithiocarbamate (ZDEC), zinc dimethyldithiocarbamate (ZDMC), zinc dibenzyl dithiocarbamate (ZBED), sodium diethyl dithiocarbamate (SDEC), and sodium dibutyldithiocarbamate (SDBC).

As noted above, the compounded SIS latex composition may include one or more sulfur donors. In some instances, the sulfur donor may also be classified as or recognized in the field as being an accelerator. In some embodiments, useful sulfur donors can include one or more thiurams, such as dipentamethylenethiuram hexasulfide (DPTTH), dipentamethylenethiuram tetrasulfide (DPTT), tetramethylthiuram monosulfide (TMTM), tetramethylthiuram disulfide (TMTD), tetraethylthiuram disulfide (TETD), and tetrabenzylthiuram disulfide (TBzTD). Additionally, or alternatively, other types of sulfur donors may also be utilized. For example, 4,4'-dithiodimorpholine (DTDM), thiocarbamyl sulfonamide, and N-oxydiethylene thiocarbamyl-N-oxydiethylene sulfenamide (OTOS) may be utilized in some embodiments. The use of such materials can be beneficial in that the sulfur included in the sulfur donor compounds is not free sulfur that can contribute to potential allergies. Additionally, disulfide (S—S) bonds produced during curing (i.e., cross-linking) when using curing materials that include free/elemental sulfur are very weak and are susceptible to breakage from exposure to heat or stress. By using sulfur donors that include bulky, alkyl groups, breakage when exposed to heat or stress can be significantly reduced. The presently disclosed compositions and methods further reduce the possibility of surface bloom and also can provide significantly improved heat resistance and aging stability.

A single curing accelerator or a mixture of two or more curing accelerators may be used in the compounded SIS latex composition in a total amount based upon a composition including 100 parts per hundred rubber (phr) of the SIS latex. For example, in some embodiments, a single curing accelerator may be used in an amount of about 0.01 to about 5.0 phr, about 0.02 to about 4.0 phr, about 0.1 to about 3.0 phr, or about 0.5 to about 2.0 phr. In other embodiments, a single curing accelerator may be used in an amount of about 0.1 to about 5.0 phr, about 0.2 to about 4.5 phr, or about 0.4 to about 4.0 phr. In further embodiments, a total amount of all curing accelerators in the SIS latex composition can be about 0.2 to about 8.0 phr, about 0.3 to about 6.0 phr, about 0.4 to about 5.0 phr, about 0.5 to about 4.0 phr, or about 1.0 to about 3.0 phr. In some embodiments, a sulfur donor may be considered to be a cure accelerator, and the amount of a sulfur donor may be within the above-recited ranges for single cure accelerators and/or for total cure accelerators. Alternatively, the above-discussed ranges may be applied individually to components utilized as accelerators and to components utilized as sulfur donors.

In one or more embodiments, a compounded SIS latex composition useful according to the present disclosure can comprise SIS polymer and optionally a further polymer, an accelerator, and a sulfur donor. In some embodiments, a compounded SIS latex composition may consist essentially of or consist of SIS polymer and optionally a further polymer, an accelerator, and a sulfur donor. A compounded SIS latex composition according to the present disclosure, however, can further comprise one or more additional components that can be useful, for example, to assist in resisting aging (and thus maintaining stability of the end product) and/or to provide additional, useful properties to the formed elastomeric article. As non-limiting examples, further materials such as surfactant(s), antioxidant(s), rheological stabilizer(s), filler(s), and smoothing agent(s) may be included in the compounded SIS latex composition. Accordingly, in one or more embodiments, a compounded SIS latex composition according to the present disclosure may comprise, consist essentially of, or consist of SIS polymer and optionally a further polymer, an accelerator, a sulfur donor, and an antioxidant; a compounded SIS latex composition according to the present disclosure may comprise, consist essentially of, or consist of SIS polymer and optionally a further polymer, an accelerator, a sulfur donor, and a rheological stabilizer; a compounded SIS latex composition according to the present disclosure may comprise, consist essentially of, or consist of SIS polymer and optionally a further polymer, an accelerator, a sulfur donor, an antioxidant, and a rheological stabilizer; a compounded SIS latex composition according to the present disclosure may comprise, consist essentially of, or consist of SIS polymer and optionally a further polymer, an accelerator, a sulfur donor, and a surfactant; a compounded SIS latex composition according to the present disclosure may comprise, consist essentially of, or consist of SIS polymer and optionally a further polymer, an accelerator, a sulfur donor, a surfactant, and an antioxidant; a compounded SIS latex composition according to the present disclosure may comprise, consist essentially of, or consist of SIS polymer and optionally a further polymer, an accelerator, a sulfur donor, a surfactant, an antioxidant, and a rheological stabilizer; and/or a compounded SIS latex composition according to the present disclosure may comprise, consist essentially of, or consist of SIS polymer and optionally a further polymer, an accelerator, a sulfur donor, a surfactant, an antioxidant, and one or more of a rheological stabilizer, a filler, and a smoothing agent. It is understood that recitation of "a" component above does not exclude the presence of a plurality of any one or more of the noted components unless the context specifically indicates that only a single instance of the noted component is to be utilized. Moreover, one or more components may be expressly excluded from such example compositions.

A variety of surfactants may be utilized in the present compositions, including cationic surfactants, anionic surfactants, and amphoteric surfactants. In some embodiments, one or more amphoteric surfactants in particular may be included with the SIS latex. Amphoteric surfactants are recognized as being zwitterionic and thus include both positive and negative charges, and any such material may be utilized according to the present disclosure. Useful amphoteric surfactants may include alkyl substituted amino acids, betaines, and amine oxides. For example, monosodium N-lauryl-beta-iminodipropionic acid, may be particularly useful in the present compositions. Non-limiting examples of alternative types of surfactants that may be utilized include potassium laurate, sodium salt of sulfated methyl oleate, and sodium dodecylbenzene sulfonate (SDBS). The amount of surfactant(s) included in the present SIS latex compositions can be in the range of about 0.01 to about 4 phr, about 0.05 to about 3.5 phr, about 0.1 to about 3.0 phr, or about 0.2 to about 2.0 phr.

Various types of antioxidants may likewise be utilized in the present SIS latex compositions. Non-limiting examples of antioxidants that may be used include a butylated reaction product of p-cresol and dicylopentadiene that is available under the name Bostex 24 and a variety of mercaptoimidazole compounds, such as 2-mercaptobenzimidazole (MBI), 2-mercaptotoluimidazole (MTT), 2-mercapto toluimidazole (MTI), a zinc salt of 2-mercaptobenzimidazole (ZMBI), a zinc salt mercaptotoluimidazole (ZNTI), and the like. The amount of antioxidant(s) (individually or in total) included in the present SIS latex compositions can be in the range of about 0.01 to about 4 phr, about 0.05 to about 3.5 phr, about 0.1 to about 3.0 phr, or about 0.2 to about 2.0 phr.

A non-limiting example of fillers that may be utilized includes fumed silicas or dispersions thereof, such as available under the tradename Cab-o-sperse®. A non-limiting example of smoothing agents that may be utilized include proteins, such as casein. The amount of filler(s) and/or smoothing agent(s) included in the present SIS latex compositions (individually or in total) can be in the range of about 0.01 to about 4 phr, about 0.05 to about 3.5 phr, or about 0.1 to about 3.0 phr.

In various embodiments, elastomeric articles may be prepared by conventional methods, such as dipping one or more formers into a liquid polymer composition, such as defined herein, one or more times to form one or more layers of the polymer composition on the former. While suitable elastomeric articles may be formed using a variety of polymer compositions utilizing various combinations of the possible ingredients described herein, it has been found herein that addition of one or more rheology modifiers can be particularly useful to improve the dipping profiled so that the tensile properties and the overall aesthetics of the formed product are not solely dependent upon the rheological properties of the liquid composition arising from the total solids content of the liquid composition. In other words, while combination of the polymer(s) components, any surfactants, any antioxidants, and any of the further compounds described herein (i.e., to provide a compounded SIS formulation) may be effective to form an elastomeric article with desired properties, the compounded SIS formulation may not exhibit properties in the liquid state that allow for consistency in the manufacturing process so that film properties are substantially uniform from one item to the next. The present disclosure can overcome such consistency issues, when needed, through addition of one or more rheological stabilizers. For example, while natural rubber and substantially pure synthetic polyisoprene latex compositions have previously been used because of their stability, the use of further polymers for forming elastomeric articles can be challenging due to low stability and/or inconsistent dipping results, as noted above. Initial testing according to the present disclosure found that while a compounded SIS formulation was effective for forming elastomeric articles, inconsistent film coverage on the film former hindered the ability to provide articles with consistently achieved properties that are discussed herein and also led to unacceptable defect occurrence and unacceptable scrap rates. According to the present disclosure, such unacceptable results can be overcome in a variety of manners.

As further described below, such problems with inconsistency may be addressed in some embodiments through specific control of process conditions. Likewise, such problems may be addressed, at least in part, through the specific use of amphoteric surfactants and/or specific combinations of cure accelerators. In one or more embodiments, improved dipping profile (and thus consistent production of elastomeric articles with desired properties) may be achieved through addition of at least one rheological stabilizer. Such components may be beneficial to impart stability to the compounded SIS formulation by, for example, improving pick-up of the compounded SIS formulation on the surface of the former. Improved "pick-up" can mean imparting greater uniformity of the ultimate coating layer, thus avoiding thin spots or even voids in the coating layer. Useful rheological stabilizers can be any additive, particularly a polymer additive, that is adapted to or configured to improve film thickness uniformity without significantly adversely affecting other film properties, such as tensile strength and/or tensile modulus. This can be achieved, for example, by improving the viscosity profile, flow properties, and similar rheological properties of the liquid, compounded SIS formulation to be applied to a former. Particularly useful rheological stabilizers can include one or more materials categorized as a hydrophobically modified alkali swellable emulsion ("HASE") polymer.

Known HASE materials that may be utilized according to the present disclosure include materials which preferably include structural units of a) an acrylate, for example ethyl acrylate, butyl acrylate, or ethylhexyl acrylate, preferably ethyl acrylate; b) an acid, preferably acrylic acid, methacrylic acid, itaconic acid, or phosphoethyl methacrylate, preferably acrylic acid or methacrylic acid; and c) an alkylated ethoxylate monomer, preferably an alkylated ethoxylate acrylate or methacrylate. In some embodiments, useful HASE polymers include materials comprising ethyl acrylate, methacrylic acid, and hydrophobically modified (e.g., with $C_{22}$ behenyl pendant groups) methacrylate with 25 moles of ethoxylation. Such materials can function synergistically with surfactants. In a non-limiting example embodiment, a suitable HASE material is available under the name Novethix™ L-10 and is an acrylates/beheneth-25 methacrylate copolymer. In one or more embodiments, a single HASE material or a total HASE material content in an SIS latex composition can be in the range of about 0.01 to about 1.0 phr, about 0.01 to about 0.50 phr, about 0.01 to about 0.20 phr, or about 0.02 to about 0.05 phr.

In one or more embodiment, SIS latex compositions useful herein may include the SIS latex emulsion alone or may include the SIS latex emulsion in combination with one or more further components described above. As non-limiting examples, the present disclosure encompasses at least the following compositions (wherein the absence of any component otherwise mentioned herein may encompass the express exclusion of such component): SIS latex dispersion alone; SIS latex dispersion and one or more amphoteric surfactants; SIS latex dispersion and one or more cure accelerators; SIS latex dispersion and one or more sulfur donors; SIS latex dispersion, one or more amphoteric surfactants, and one or more cure accelerators; SIS latex dispersion, one or more amphoteric surfactants, and one or more sulfur donors; SIS latex dispersion, one or more cure accelerators, and one or more sulfur donors; SIS latex dispersion, one or more amphoteric surfactants, one or more cure accelerators, and one or more sulfur donors; SIS latex dispersion, one or more amphoteric surfactants, one or more cure accelerators, one or more sulfur donors, and one or more antioxidants. Optionally, any of the foregoing may include one or more fillers and/or one or more smoothing agents and/or one or more viscosity modifiers. Preferably, the SIS latex composition will have a solid content as noted previously. Likewise, preferably, the SIS latex composition will utilize SIS polymer having a styrene content as noted previously. As non-limiting examples, suitable SIS latex compositions may include one or more of the following materials in the noted ranges, and it is understood that the noted ranges are exemplary only, and may be modified in light of the further ranges otherwise described herein. For example, an SIS latex composition may comprise approximately 100 phr of the SIS latex emulsion at the desired solid content, about 0.1 to about 5.0 phr of one or more cure accelerators, about 0.01 to about 2.0 phr of one or more surfactants, about 0.1 to about 5.0 phr of one or more sulfur donors, and about 0.01 to about 2.0 phr of one or more antioxidants. Optionally, an SIS latex composition may comprise about 0.01 to about 0.5 phr of one or more fillers and/or about 0.01 to about 0.5 phr of one or more smoothing agents and/or about 0.01 to about 0.5 phr of one or more viscosity modifiers. The foregoing are provided as example embodiments and should not be construed as excluding combinations of components and concentrations in ranges otherwise described herein unless expressly noted.

SIS latex compositions as described above can be used as otherwise described herein in preparing one or more products, such as an elastomeric article (e.g., gloves, condoms, or similar film-like, elastomeric articles). Beneficially, the formed products can be substantially streak-free, can be compatible with a wide range of materials that are commonly combined with such articles (e.g., powders for gloves and lubricants for condoms), can exhibit improved case of removal from formers during production of the products, and can exhibit reduced or no yellow coloration. Thus, the compositions and products may exhibit at least a certain level of whiteness as observable utilizing a colorimeter. In addition, elastomeric articles prepared according to the present disclosure utilizing SIS latex compositions as described herein can exhibit a variety of physical properties at specifically desirable performance levels.

An elastomeric article according to the present disclosure in particular can exhibit a tensile strength of about 20 MPa or greater, about 22 MPa or greater, about 25 MPa or greater or about 28 MPa or greater (such as in the range of about 20 MPa to about 50 MPa, about 22 MPa to about 40 MPa, or about 25 MPa to about 38 MPa). Likewise, an elastomeric article according to the present disclosure can exhibit a tensile modulus at 500% elongation that is less than 2.75 MPa, less than 2.25 MPa, less than 2.0 MPa, less than 1.75 MPa, or less than 1.50 MPa (such as in the range of about 0.50 to about 2.70, about 0.50 to about 2.20, about 0.75 to about 2.10, about 1.0 to about 2.0, or about 1.1 to about 1.8. Tensile strength and tensile modulus can be measured in accordance with American Society for Testing and Materials (ASTM) D412.

Tear strength (or tear resistance) can also be used as an indicator of appropriate strength and article integrity. More particularly, tear strength/tear resistance may be defined as the average force required to propagate a tear in the article divided by the thickness of the article. This value thus can incorporate a measured tear force, which is the average force required for the article to completely tear. Because the unique properties of elastomeric articles, such as the SIS articles described herein, tear force may be recited as an average since the actual values (highs and lows) will vary across the total article. In some embodiments, an elastomeric article according to the present disclosure can have a tear strength of at least 1.5 N/mm, at least 2 N/mm, or at least 2.2 N/mm (e.g., up to a maximum of about 20 N/mm or about 15 N/mm). In further embodiments, tear strength can be about 2 N/mm to about 20 N/mm, about 2.2 N/mm to about 15 N/mm, about 2.5 N/mm to about 12 N/mm, or about 3 N/mm to about 10 N/mm. Tear strength can be evaluated using ASTM D624-000.

Elastomeric articles according to the present disclosure further can be defined in relation to the elongation at break. For example, the present elastomeric articles can exhibit an elongation at break of about 1000% or greater, about 1050% or greater, or about 1100% or greater (such as in the range of about 1000% to about 1500%, about 1050% to about 1400%, or about 1100% to about 1300%). Physical properties exhibited by example embodiments of elastomeric articles as well as methods of preparing such articles and example compositions used in preparing such articles are further provided in the Examples appended hereto.

Physical characteristics of an elastomeric article described herein (such as tensile strength, tensile modulus, and elongation at break) can be derived, in some embodiments, from the specific combination of materials utilized in forming the articles. In further embodiments, physical properties may be derived, at least in part, from the processing steps used in forming the elastomeric articles. For example, stability of the elastomeric article may directly relate to the type and amount of surfactant that is utilized (e.g., the specific utilization of an amphoteric surfactant) and/or total solids level of the SIS latex composition and/or the relative styrene concentration in the SIS polymer. Film strength may be directly related to the combination of accelerators that are used and the total concentration of accelerators and/or to the uniformity of the produced film. Film elasticity may be directly related to the nature of the physical and chemical crosslinking that is achieved during film formation, including the level of prevulcanization that is achieved and/or the final cure level that is achieved. Film clarity may be directly related to the formulation stability, the uniformity of the film, and the combination of accelerators and concentration of accelerators that are used.

In some embodiments, the elastomeric articles may be characterized in relation to dynamic mechanical analysis (DMA), such as the testing described in Example 9 herein. DMA testing can be utilized to provide a Young's modulus (E') that is indicative of mechanical properties of the article when under a substantially low degree of stretch, and this can be indicative of high film quality that is analogous to strength testing that is carried out at higher degrees of stretching (e.g., tensile strength). Elastomeric articles according to the present disclosure may have a Young's modulus (E') that is less than 1 MPa at a frequency of 1 Hz and that is greater than 1 MPa at a frequency of 21.5 Hz. For example, the Young's modulus (E') at 1 Hz may be less than 1 MPa but greater than 0.8 MPa, and the Young's modulus (E') at 21.5 Hz may be greater than 1.05 MPa, greater than 1.1 MPa, or greater than 1.15 MPa.

Physical properties of the elastomeric articles or films that are produced according to the present disclosure may likewise relate to the average thickness of the articles/films. The presently disclosed compositions may be particularly useful in forming relatively thin-walled structures that still exhibit the overall strength (e.g., at least a minimum tensile strength and/or tear strength) and softness (e.g., below a maximum tensile modulus) that is desired. In one or more embodiments, physical characteristics defined herein may relate to an elastomeric article having an average thickness of less than 0.1 mm, less than 0.09 mm, or less than 0.08 mm (e.g., down to a minimum thickness of about 0.01 mm). Preferably, the elastomeric articles may have a thickness of about 0.04 mm to about 0.09 mm, about 0.045 mm to about 0.085 mm, or about 0.06 mm to about 0.08 mm.

In one or more embodiments, the present disclosure further provides for methods of preparing an elastomeric article. The methods may include a plurality of steps including mixing of polymer composition components, one or more steps wherein a former of other mold is dipped or otherwise coated with one or more coatings or layers of polymer composition to form a film of a desired thickness, and a curing step wherein the formed film is processed to be in a substantially finished form (e.g., crosslinked or otherwise solidified to form a unitary article of manufacture). Optionally, one or more drying steps may be utilized. Further, suitable processing equipment may be used as needed to provide for the necessary processing steps, including formers, dip tanks, heating equipment, fans, conveyers, and the like may be utilized.

A SIS latex dispersion may be obtained from a supplier in a higher solid content than is desired for the end products. Accordingly, a method of manufacture of an elastomeric article can include diluting a SIS latex dispersion (e.g., using deionized water or the like) to the desired solid content. The optionally diluted SIS latex dispersion may be ready for use as a formulation for forming a film. In some embodiments, where one or more additives may be desired, the specific additives may be added sequentially or simultaneously to the SIS latex dispersion to form the polymer composition. Where surfactants and accelerators are utilized, these in particular may be added together to the SIS latex dispersion and stirred for a time to reach a substantially homogeneous dispersion of the materials. Antioxidant may specifically be added to the polymer composition after addition of the further components, such as within a few hours of the start of any dipping or other coating process. The polymer composition may be filtered prior to being transferred to a dip tank or storage tank for storage for a time suitable for de-aeration of the mixture. For example, the polymer composition may be filtered using a 200 μm filter (e.g., suitable to filter out particles having a size greater than 200 μm) or a differently sized filter (e.g., suitable to filter out particles having a size that is greater than 150 μm, greater than 175 μm, greater than 200 μm, or greater than 225 μm).

In some embodiments, a method for preparing an elastomeric article may particularly be a binary process, which can indicate that two separate formulations are utilized or that at least two separate formulations are utilized. A former or other mold then may be dipped or otherwise coated at least once with each of the separate formulations in any order, optionally being at least partially dried between separate dipping or coating procedures. A Formulation A, for example, may comprise a SIS polymer (e.g., a SIS latex dispersion), one or more cure accelerators, one or more surfactants, and optionally one or more cure agents and/or activators, and a Formulation B, for example, may comprise a SIS polymer and one or more surfactants and may expressly exclude any cure accelerators and/or cure agents. Such binary dipping process can be particularly useful to provide improved control over the final cure of the SIS latex film (e.g., the elastomeric article). This is achieved, as noted above, by separating the SIS polymer (and optional combinatory polymer—e.g., NRL) into separate dip tanks, one including compounded polymer(s) that can cure and chemically crosslink, and another including only the polymer(s) and stabilizing agents that can physically crosslink during the final curing. A such, physical and chemical crosslinking can be balanced without the need for prevulcanization though heating of the compounded SIS polymer formulation. This can be particularly useful since compounded SIS formulations can over-cure without close monitoring of the prevulcanization temperature, which can adversely affect the desired properties of the formed, elastomeric article.

In an example embodiment, methods for preparing an elastomeric article can comprise forming a film on a former or other mold using two separate formulations having different overall compositions, each of the two separate formulations comprising a SIS polymer composition or latex dispersion. The two (or at least two) separate formulations are separate and have different overall compositions such that the binary process excludes processes wherein a formed may simply be dipped multiple times in a single composition. Rather, the separate and different formulations can vary in the components included therein or excluded therefrom, can vary in the concentration of components included therein, can vary in the solid content of the formulation, or in any combination of such variations. In some embodiments, the separate and different formulations can differ in that one of the separate and different formulations can expressly include one or more cure accelerators, and another of the separate and different formulations can expressly exclude one or more cure accelerators and/or cure agents.

The binary method of forming an elastomeric article can comprise sequential dipping or coating of a former or other mold using separate containers that separately contain the two (or more) separate formulations to form a film on the former or mold. As such, coating or dipping can be carried out as two or more individual coating or dipping actions that are performed separately and sequentially. If desired, the separate and sequential coating or dipping actions may be separated by a drying period. Thus, a first coating or dipping action may be carried out to begin forming of a film, the partial film may be at least partially dried during the drying period, and a second coating or dipping action may be carried out to further form or complete forming of the film. While the individual coating or dipping actions may be characterized as forming multiple layers, as already described above, it is understood that the final, elastomeric article to be prepared is preferably a substantially, thin-film type article having an average film thickness, wherein the film is a unitary structure, and individual "layers" are not separable from each other (i.e., there can be no de-lamination of layers). Individual coating or dipping actions thus preferentially are adapted to or configured to add to an overall average thickness of the film that is formed on the former or other mold without forming physically separable layers.

An individual drying period may be carried out for a defined time under defined conditions. For example, a drying period may continue for a time of about 1 minute or greater, about 2 minutes or greater, or about 3 minutes or greater (such as about 1 minute to about 10 minutes or about 2 minutes to about 8 minutes). Drying conditions may be, for example, at a temperature of about 50° C. or greater, about 70° C. or greater, or about 80° C. or greater (such as about 50° C. to about 110° C., about 70° C. to about 110° C., or about 80° C. to about 110° C.). Drying may be carried out between individual coating or dipping actions and/or may be carried out after completion of all coating or dipping actions.

After all of the coating or dipping actions have been carried out, the method can further include curing the film. In some embodiments, curing can be carried out at a temperature of about 100° C. or greater or about 110° C. or greater (such as a temperature range of about 100° C. to about 140° C. or about 110° C. to about 130° C.). The curing time can vary can be, for example, carried out for a time of about 5 minutes or greater or about 10 minutes or greater (such as about 5 minutes to about 30 minutes or about 10 minutes to about 20 minutes).

In an example embodiment, a method for preparing an elastomeric article in particular may comprise providing a Formulation A comprising a SIS polymer, one or more surfactants, and one or more cure accelerators and providing a Formulation B comprising a SIS polymer and a surfactant but excluding any cure accelerators. The method can further comprise dipping a former into one of Formulation A and Formulation B to form a film of the respective Formulation on the former, at least partially drying the film on the former, dipping the forming into the other of Formulation A and Formulation B to further form a film of the respective Formulation on the former, and curing the film including Formulation A and Formulation B.

In one or more embodiments, a method for preparing an elastomeric article according to the present disclosure may utilize a single dipping formulation of the SIS latex composition. As such, an elastomeric article may be prepared by first forming a compounded latex composition including the SIS polymer and one or more further components as described herein. As a non-limiting example, the compounded latex composition can comprise a polystyrene-polyisoprene-polystyrene (SIS) latex, at least one sulfur donor, and at least one dithiocarbamate accelerator. Optionally, one or more amphoteric surfactants, one or more antioxidants, one or more fillers, and/or one or more smoothing agents may be included. The compounded latex composition may be subjected to conditions suitable for prevulcanization of the composition to a desired level of prevulcanization or crosslink density. Thereafter, a former may be dipped into the prevulcanized compounded latex composition to form at least one layer of the prevulcanized compounded latex composition thereon. In some embodiments, the former may be dipped a single time to form a single layer, or the former may be dipped twice to form two layers, or the former may be dipped three times to form three layers, or even more dipping iterations may be carried out. Where multiple dipping steps are utilized, the formed layer may be at least partially dried before carrying out the next step in the process. The layer(s) of the prevulcanized compounded latex composition may be cured to form the final elastomeric product, which them may be removed from the former using any suitable method in the field.

In some embodiments, the present method may be carried out under defined conditions that are effective to provide desired properties in the finished, elastomeric article. For example, in some embodiments, desired properties may be achieved by utilizing specific prevulcanization conditions. For example, it can be useful for prevulcanization to be carried out for maturing the composition through crosslinking. Since the present compositions may be expressly free of any free sulfur or soluble sulfur and rather utilizes a sulfur donor, specific prevulcanization conditions may be useful to ensure that the composition is crosslinked to the correct crosslink density prior to dipping. For example, maturing or prevulcanization can be carried out in a temperature range of about 25° C. to about 40° C. for a time of about 12 hours to about 48 hours. In some embodiments, the temperature for prevulcanization may be substantially steady throughout the prevulcanization time (e.g., varying in temperature by no more than 2° C. or no more than 1° C.). In some embodiments, however, the prevulcanization may be split into a plurality of temperatures for defined lengths of time. For example, prevulcanization may be carried out for a first time period at a first temperature and then for a second time period at a second, lower temperature. A first, higher temperature range may be about 32° C. to about 38° C., about 33° C. to about 37° C., or about 34° C. to about 36° C. A second, lower temperature range may be about 26° C. to about 32° C., about 27° C. to about 31° C., or about 28° C. to about 30° C. The "higher" and "lower" temperature ranges preferably are separated by at least 2° C., at least 3° C., or at least 4° C. Maturing the SIS latex composition to achieve prevulcanization may be carried out such that the time of prevulcanization at the higher temperature is less than the time of prevulcanization at the lower temperature. For example, prevulcanization at the higher temperature may be for a time of about 0.5 hours to about 18 hours, about 1 hour to about 12 hours, or about 1.5 hours to about 8 hours. Prevulcanization at the lower temperature may be, for example, for a time of about 2 hours to about 36 hours, about 3 hours to about 30 hours, or about 8 hours to about 24 hours.

Indication that the desired level of prevulcanization has been achieved may, in some embodiments, be identified in relation to one or more measurable properties of the compounded latex composition prior to dipping. For example, crosslinking density of the prevulcanized, compounded latex composition may be measured using the relaxed modulus test. The method for measuring relaxed modulus was originally published by Gorton and Pendle (Natural Rubber Technology. 1976, 7 (4), 77-81). One method for evaluating relaxed modulus (or relaxation modulus) can include the following steps: prepare a tube-shaped film of the latex composition (e.g., by dipping a glass tube or similar structure into the latex composition and then drying the formed film; rolling the tube shaped film to form a ring and removing the ring from the former; weighing the formed ring to find its mass (M in grams); placing the ring on the mounts of a suitable tensile tester and stretching the ring to 100% extension for one minute; measuring the load in Newtons exerted by the ring after the one minute; and using the load reading and the mass of the ring to calculate the relaxed modulus in MPa according to the following formula:

$$\text{Relaxed Modulus } (MPa) = (F \times d \times C)/2M$$

wherein F is the load in Newtons exerted by the ring after on minute at 100% extension, d is the density of the latex ring in grams per cubic centimeter, C is the external circumference of the dipping tube in centimeters, and M is the mass of the latex ring in grams. Preferably, relaxed modulus will be measured on a plurality of samples and the mean taken as the measured value. Such testing can be carried out, for example, using the a RRIM Relaxed Modulus Tester, Model M403, available from the Malaysian Rubber Board. Likewise, such testing may be carried out using a TA.XT Plus Texture Analyzer equipped with a 5 kilogram load cell.

Prevulcanization according to the present disclosure preferably can be carried out until a defined relaxed modulus value is obtained. In one or more embodiments, the desired relaxed modulus can be in a range of about 0.50 to about 0.61, about 0.51 to about 0.60, about 0.52 to about 0.59, about 0.53 to about 0.58, or about 0.54 to about 0.57. Achieving a relaxed modulus value within these ranges can be a useful indicator that the proper balance of chemical and physical crosslinking has been achieved for the compounded SIS polymer formulation. While relaxed modulus values outside of these ranges may not hinder successful formation of an elastomeric article, maintaining relaxed modulus values within these ranges can ensure that the film properties (e.g., tensile strength and modulus) will consistently be within the desired ranges otherwise described herein.

In one or more embodiments, desired properties may be achieved by utilizing specific drying conditions during dipping. In certain embodiments, it can be desirable for drying to be carried out after a dipping step, prior to a further dipping step and/or prior to curing. Drying may be carried out in a temperature range of about 80° C. to about 120° C. or about 85° C. to about 115° C. Drying in this temperature range can be for a time of about 1 minute to about 10 minutes, about 2 minutes to about 8 minutes, or about 3 minutes to about 7 minutes. In some embodiments, two dipping steps can be utilized, and drying after the respective dipping steps can be at different temperatures. For example, drying after a first dipping step can be at a temperature that is lower than the temperature of a second dipping step. A first, lower temperature range may be about 80° C. to about 100° C., about 85° C. to about 95° C., or about 88° C. to about 92° C. A second, higher temperature range may be about 100° C. to about 120° C., about 105° C. to about 115° C., or about 108° C. to about 112° C. The "higher" and "lower" temperature ranges preferably are separated by at least 2° C., at least 3° C., or at least 4° C.

EXPERIMENTAL

The present disclosure is more fully illustrated by the following examples, which are set forth to illustrate certain embodiments of the present disclosure and are not to be construed as limiting thereof.

Example 1—Preparation of Synthetic Poly(Styrene-Isoprene-Styrene) Latex Composition An aqueous poly(styrene-isoprene-styrene) latex composition having a solid content of 65% was obtained from Kraton Polymers and was diluted to approximately 50% solid content using deionized water. Surfactant(s) and cure accelerator(s) were added to the latex mixture and stirred about 100 to 150 rpm at room temperature overnight. The compounded latex was filtered using a 200 μm filter and left in a dip tank overnight to remove air bubbles. Antioxidant(s) were added to the composition approximately two hours prior to starting of dipping.

Example 2—Preparation of Latex Articles

Latex articles were prepared utilizing the composition prepared according to Example 1. The latex articles were prepared by performing two dipping actions. A first dip in the dip tank was carried out at a withdrawal speed of about 0.2 to 0.4 inches per second to obtain the desired film thickness and oven dried at about 90° C. for about 5 minutes. A second dip in the dip tank was carried out at a withdrawal speed of about 0.2 to 0.4 inches per second to obtain the desired film thickness and oven dried at about 90° C. for about 5 minutes. The final film was oven cured at about 120° C. for about 15 minutes. The formed elastomeric latex article was removed from the former using a corn starch slurry and air dried.

Example 3—Effect of Accelerators on Physical Properties of Elastomeric Latex Articles Synthetic SIS latex compositions and elastomeric latex articles were prepared according to the methods of Example 1 and Example 2 utilizing varying accelerator components and amounts as seen in Tables 1-3 below. Tensile properties for the different articles are also shown. As can be seen, the type of accelerator and the concentration utilized can affect the level of chemical crosslinking that is achieved.

TABLE 1

| Formulation (in phr) | | Control | Accelerator (1.3 phr) | Accelerator (1.5 phr) | Accelerator (1.7 phr) |
|---|---|---|---|---|---|
| Latex | SIS | 100 | 100 | 100 | 100 |
| Surfactant | Manawet ™ 172 | 0.5 | 0.5 | 0.5 | 0.5 |
| Cure Agent | Sulfur | 0 | 0 | 0 | 0 |
| Cure Activator | Zinc Oxide | 0 | 0 | 0 | 0 |
| Cure Accelerator | ZDEC (Bostex 561) | 0 | 0.52 | 0.6 | 0.68 |
| | DPTTH (Bostex 224) | 0 | 0.78 | 0.9 | 1.02 |
| Antioxidant | Wingstay ® L | 0.5 | 0.5 | 0.5 | 0.5 |
| Tensile Properties | Tensile (MPa) | 19.42 | 24.9 | 28 | 25.4 |
| | Modulus@500% (MPa) | 1.04 | 1.52 | 1.59 | 1.75 |
| | Elongation (%) | 1419 | 1335 | 1358 | 1288 |

TABLE 2

| Formulation (in phr) | | Accelerator (2.0 phr) | Accelerator (2.5 phr) | Accelerator (3.0 phr) | Accelerator (4.0 phr) |
|---|---|---|---|---|---|
| Latex | SIS | 100 | 100 | 100 | 100 |
| Surfactant | Manawet ™ 172 | 0.5 | 0.5 | 0.5 | 0.5 |
| Cure Agent | Sulfur | 0 | 0 | 0 | 0 |
| Cure Activator | Zinc Oxide | 0 | 0 | 0 | 0 |
| Cure Accelerator | ZDEC (Bostex 561) | 0.8 | 1.0 | 1.2 | 1.5 |
| | DPTTH (Bostex 224) | 1.2 | 1.5 | 1.8 | 2.5 |
| Antioxidant | Wingstay ® L | 0.5 | 0.5 | 0.5 | 0.5 |
| Tensile Properties | Tensile (MPa) | 28.2 | 26 | 29.8 | 21.95 |
| | Modulus@500% (MPa) | 1.93 | 2.3 | 2.7 | 3.27 |
| | Elongation (%) | 1300 | 1233 | 1181 | 1079 |

TABLE 3

| Formulation (in phr) | | Control | Bostex 561/224 | Bostex 909 |
|---|---|---|---|---|
| Latex | SIS | 100 | 100 | 100 |
| Surfactant | Manawet ™ 172 | 0.5 | 0.5 | 0.5 |
| Cure Agent | Sulfur | 0 | 0 | 0 |
| Cure Activator | Zinc Oxide | 0 | 0 | 0 |
| Cure Accelerator | ZDEC (Bostex 561) | 0 | 0.6 | 0 |
| | DPTTH (Bostex 224) | 0 | 0.9 | 0 |
| | ZDEC + DPTT (Bostex 909) | 0 | 0 | 1.5 |
| Antioxidant | Wingstay ® L | 0.5 | 0.5 | 0.5 |
| Tensile Properties | Tensile (MPa) | 19.42 | 28 | 26.4 |
| | Modulus@500% (MPa) | 1.04 | 1.59 | 1.7 |
| | Elongation (%) | 1419 | 1358 | 1273 |

Example 4—Effect of Cure Agent and Cure Activator on Physical Properties of Elastomeric Latex Articles Synthetic SIS latex compositions and elastomeric latex articles were prepared according to the methods of Example 1 and Example 2 with and without the use of sulfur cure agent and zinc oxide cure activator to evaluate the effect on tensile properties. The formulations and testing results are shown in Table 4 below. As seen therein, the presence of sulfur and zinc oxide tended to increase the tensile modulus while also decreasing the tensile strength. This result therefore is surprising in that, in conventional latex compositions (e.g., natural rubber and/or synthetic polyisoprene), sulfur and zinc oxide are used to increase crosslinking in order to improve tensile strength. The present testing, however, showed that it is possible to achieve suitable tensile properties while excluding sulfur and zinc oxide and thus being substantially free or completely free of Type I and Type IV allergens.

TABLE 4

| Formulation (in phr) | | Control | Without Sulfur/ZnO | With Sulfur/ZnO | With Sulfur/ZnO |
|---|---|---|---|---|---|
| Latex | SIS | 100 | 100 | 100 | 100 |
| Surfactant | Manawet ™ 172 | 0.5 | 0.5 | 0.5 | 0.5 |
| Cure Agent | Sulfur | 0 | 0 | 0.5 | 0.5 |
| Cure Activator | Zinc Oxide | 0 | 0 | 0.5 | 0.5 |
| Cure Accelerator | ZDEC (Bostex 561) | 0 | 0.6 | 0.6 | 1.2 |
| | DPTTH (Bostex 224) | 0 | 0.9 | 0.9 | 1.8 |
| Antioxidant | Wingstay ® L | 0.5 | 0.5 | 0.5 | 0.5 |
| Tensile Properties | Tensile (MPa) | 19.42 | 28 | 25.63 | 29.8 |
| | Modulus@500% (MPa) | 1.04 | 1.59 | 2.33 | 2.7 |
| | Elongation (%) | 1419 | 1358 | 1267 | 1181 |

Example 5—Effect of Viscosity Modifier on Physical Properties of Elastomeric Latex Articles Synthetic SIS latex compositions and elastomeric latex articles were prepared according to the methods of Example 1 and Example 2 with and without the use of a viscosity modifier to evaluate the effect on tensile properties. The formulations and testing results are shown in Table 5 below. The addition of the rheological stabilizer is thus effective to improve dipping profile without adversely affecting the desired properties of the finished product.

TABLE 5

| Formulation (in phr) | | Control | Without Novethix-L10 | With Novethix-L10 |
|---|---|---|---|---|
| Latex | SIS | 100 | 100 | 100 |
| Surfactant | Manawet ™ 172 | 0.5 | 0.5 | 0.5 |
| Cure Agent | Sulfur | 0 | 0 | 0 |
| Cure Activator | Zinc Oxide | 0 | 0 | 0 |
| Cure Accelerator | ZDEC (Bostex 561) | 0 | 0.6 | 0.6 |
| | DPTTH (Bostex 224) | 0 | 0.9 | 0.9 |
| Antioxidant | Wingstay ® L | 0.5 | 0.5 | 0.5 |
| Viscosity Modifier | Novethix ™ L10 | 0 | 0 | 0.05 |
| Tensile Properties | Tensile (MPa) | 19.42 | 28 | 26.3 |
| | Modulus@500% (MPa) | 1.04 | 1.59 | 1.9 |
| | Elongation (%) | 1419 | 1358 | 1294 |

Example 6—Binary Process for Preparation of Synthetic SIS Latex Articles, and Evaluation of Tensile Properties Elastomeric articles can be prepared using a single dip formulation (as discussed above in Example 2); however, elastomeric articles with desirable properties likewise can be prepared using a binary dipping process that utilizes two different polymer formulations. In the present example embodiment, Formulation A (including aqueous SIS latex, surfactant, cure accelerators, and antioxidant) was prepared according to the process of Example 1. Formulation B was prepared by the same process but only included aqueous SIS latex, surfactant, and antioxidant. Formulation A was added to dip tank 1, and Formulation B was added to dip tank 2. As a comparative, Formulation C was prepared according to the process of Example 1 using aqueous SIS latex, surfactant, sulfur cure agent, zinc oxide cure activator, cure accelerators, and antioxidant. Formulation C was added to dip tank 3. The exact formulations used in dip tank 1, dip tank 2, and dip tank 3 are shown in Table 6.

The binary dipping process using Formulation A and Formulation B in dip tank 1 and dip tank 2 was carried out as follows. A former was first dipped into Formulation A in dip tank 1 at a withdrawal speed of about 0.2 to 0.4 inches per second to obtain the desired film thickness and oven dried at about 90° C. for about 5 minutes. The former with the dried film was then dipped into Formulation B in dip tank 2 at a withdrawal speed of about 0.2 to 0.4 inches per second to obtain the desired film thickness and oven dried at about 90° C. for about 5 minutes. The final film was oven cured at about 120° C. for about 15 minutes. The formed elastomeric latex article was removed from the former using a corn starch slurry and air dried. A further former was used to prepare the control article according to the process of Example 2 using Formulation C and dip tank 3. The test results are shown in Table 6.

TABLE 6

| Formulation (in phr) | | Dip Tank 3 with all components in single tank (Control) | Binary Process | |
|---|---|---|---|---|
| | | | Dip Tank 1 (Formulation A) | Dip Tank 2 (Formulation B) |
| Latex | SIS | 100 | 100 | 100 |
| Surfactant | Manawet ™ 172 | 0.5 | 0.5 | 0.5 |
| Cure Agent | Sulfur | 0.5 | 0 | 0 |
| Cure Activator | Zinc Oxide | 0.27 | 0 | 0 |
| Cure Accelerator | ZDEC (Bostex 561) | 0.6 | 0.6 | 0 |
| | DPTTH (Bostex 224) | 0.9 | 0.9 | 0 |
| Antioxidant | Wingstay ® L | 0.5 | 0.5 | 0 |
| Tensile Properties | Tensile (MPa) | 25.63 | 26.34 | |
| | Modulus@500% (MPa) | 2.33 | 1.53 | |
| | Elongation (%) | 1267 | 1367 | |

Example 7—Preparation of Synthetic SIS Latex Articles with Single Dip Tank

Condoms were prepared from compounded SIS latex compositions using varying prevulcanization and drying conditions. The formed condoms were then subjected to tensile strength testing and tensile modulus testing. The compounded SIS latex composition is shown in Table 7. The condom forming parameters and the measured properties of the formed condoms are provided in Table 8.

TABLE 7

| Component | Concentration (phr) |
|---|---|
| SIS polymer latex dispersion | 100 |
| Amphoteric surfactant | 0.5 |
| Sulfur donor | 0.9 |
| Accelerator | 0.6 |
| Antioxidant | 0.5 |

TABLE 8

| | Run 1 | Run 2 | Run 3 | Run 4 | Run 5 |
|---|---|---|---|---|---|
| Pre-Vulc. Conditions | 35° C. for 3 hrs/29° C. for 18 hrs | 35° C. for 6 hrs/29° C. for 18 hrs | 29° C. for 23 hrs | 35° C. for 17 hrs/29° C. for 23 hrs | 35° C. for 3 hrs/29° C. for 18 hrs |
| Dry 1/Dry 2 Conditions | 90° C. for 5 min/100° C. for 5 min | 90° C. for 5 min/100° C. for 5 min | 90° C. for 5 min/110° C. for 5 min | 90° C. for 5 min/100° C. for 5 min | 90° C. for 5 min/110° C. for 5 min |
| Tensile Strength (MPa) | 15.9 | 17.04 | 20.4 | 20.4 | 24.5 |
| Modulus at 500% (MPa) | 1.31 | 1.24 | 1.28 | 1.13 | 1.22 |
| Load at 500% (N) | 4.3 | 4 | 4.5 | 3.9 | 3.9 |
| Elongation (%) | 1260 | 1270 | 1290 | 1290 | 1310 |
| Relaxed Modulus | 0.56 | 0.68 | 0.70 | 0.65 | 0.56 |

Test sample 5 was also evaluated for tear strength using ASTM D624-000. Testing indicated that the sample exhibited a tear strength of 2.23 N/mm.

Example 8—Preparation of Synthetic SIS Latex Articles with Varying Styrene Content Condoms were prepared from compounded SIS latex compositions using SIS polymer with differing styrene percentages (i.e., 8%, 10%, 11%, 12.6, and 15% wt/wt styrene, based on the total weight of the SIS polymer). The remaining components of the test compositions were identical for each sample, and all samples were prepared under identical pre-vulcanization and drying conditions. Pre-vulcanization was carried out at 35° C. for 3 hours then 29° C. for 18 hours. The condoms were formed by dipping a former twice in the composition, drying the first coating 90° C. for 5 minutes, and drying the second coating at 100° C. for 5 minutes. Results of testing for tensile strength testing and tensile modulus are shown below in Table 9.

TABLE 9

| | Sample 1 | Sample 2 | Sample 3 | Sample 4 | Sample 5 |
|---|---|---|---|---|---|
| Styrene content in SIS polymer | 8% | 10% | 11% | 12.6% | 15% |
| Tensile Strength (MPa) | 4.66 | 11.1 | 10.9 | 11.5 | 24.5 |
| Modulus at 500% (MPa) | 0.98 | 1.08 | 1.13 | 1.17 | 1.22 |
| Relaxed Modulus | 0.28 | 0.36 | 0.42 | 0.49 | 0.56 |

Example 9—Dynamic Mechanical Analysis

Test samples were prepared using the composition provided in Table 7 above. Prevulcanization was carried out at 35° C. for a time of 3 hours or 6 hours. Articles were prepared by dipping the former into the SIS polymer formulation for two iterations. Drying after the first dipping was carried out for 5 minutes at 90° C., and drying after the second dipping was carried out for 5 minutes at 110° C. Dynamic mechanical analysis (DMA) was carried out on the formed articles to measure the properties of the solid articles in a manner analogous to rheology testing for liquid compositions. Young's modulus (E) was measured as an indication of the stiffness of the material as the material was stretched. Young's modulus (E) is defined as the ratio of the stress σ (force/area) to the strain ε (degree of deformation), wherein E=σ/ε. The modulus (E) can be defined by a complex expression involving storage modulus (E') and a loss modulus (E") as seen below, wherein $i=(-1)^{1/2}$ (i.e., negative to the ½ power), and E* is a representation of a vector quantity in the complex space, and derives from the oscillatory nature of the stress and strain.

$$E^* = E' + iE''$$

$$E = |E^*|$$

In DMA studies, samples were cut from the above-noted articles perpendicular to the long axis. The resulting ring was then folded to produce a sample 8 layers thick, and the sample was mounted in the DMA using the tensile apparatus. Dimensions were typically on the order of 9.5 cm long, 7.5 mm long, and 0.55 mm thick. All studies were run on a Triton Tritec 2000 DMA. Frequency dependent studies were performed in the frequency range of 0.1 to 75 Hz, using a displacement of 0.1 mm. Run temperatures at 25° C. and 37° C. were regulated by an electric furnace enclosing the sample holder. Runs at 25° C. were essentially at the ambient temperature of the laboratory. Temperature scans were performed by first cooling the sample with liquid nitrogen to a temperature of approximately −80° C. The furnace was then used to increase the temperature at a rate of 5° C./minute, up to a maximum temperature of 40° C. As in the frequency scans, a displacement of 0.1 mm was used, and the frequency was held constant at 1.0 Hz. In addition to the above, comparative samples were tested and were taken from commercial products sold under the tradenames Skyn® (formed of polyisoprene) and Trojan® Enz (formed of natural rubber). Plots of moduli E' versus frequency indicated that all tested samples prepared according to the present disclosure exhibited moduli that were greater than moduli of the comparative samples. The test results are illustrated in FIG. 1, and the DMA E' data are particularly useful for illustrating improved film properties when the film is at a relatively low degree of extension.

Use of the words "about" and "substantially" herein are understood to mean that values that are listed as "about" a certain value or "substantially" a certain value may vary by an industry recognized tolerance level for the specified value. When an industry recognized tolerance is unavailable, it is understood that such terminology may indicate that an acceptable value may be vary ±3%, +2%, or +1% from the specifically listed value. More particularly, where a temperature is disclosed, "about" or "substantially" may indicate the specifically listed temperature ±2° C., +1° C., or +0.5° C. Likewise, in some embodiments, the listed value may be exact, if desired, and variations above or below the listed value may be expressly excluded.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for preparing an elastomeric article, the method comprising:
preparing a compounded latex composition including a polystyrene-polyisoprene-polystyrene (SIS) latex, at least one sulfur donor, and at least one dithiocarbamate;
prevulcanizing the compounded latex composition at a temperature and for a time period effective to form a prevulcanized compounded latex composition having a relaxed modulus of about 0.50 MPa to about 0.61 MPa;
dipping a former into the prevulcanized compounded latex composition to form at least one layer of the prevulcanized compounded latex composition thereon; and
curing the at least one layer of the prevulcanized compounded latex composition on the former to provide the elastomeric article.

2. The method of claim 1, wherein the at least one sulfur donor is a thiuram compound.

3. The method of claim 1, wherein the at least one sulfur donor includes one or both of dipentamethylenethiuram tetrasulfide (DPTT) and dipentamethylenethiuram hexasulfide (DPTTH).

4. The method of claim 1, wherein the compounded latex composition further includes one or both of an amphoteric surfactant and an antioxidant.

5. The method of claim 1, comprising prevulcanizing the compounded latex composition at a first temperature for a first time period and then at a second, lower temperature for a second time period.

6. The method of claim 5, wherein the first temperature is in a range of about 32° C. to about 38° C., and the first time period is in a range of about 0.5 hours to about 18 hours.

7. The method of claim 5, wherein the second temperature is in a range of about 26° C. to about 32° C., and the second time period is in a range of about 2 hours to about 36 hours.

8. The method of claim 5, wherein the first temperature and the second temperature are separated by at least 2° C.

9. The method of claim 1, wherein the relaxed modulus is measurable according to a test comprising:
preparing a tube-shaped film of the prevulcanized compounded latex composition on a dipping structure;
rolling the tube shaped film to form a ring;
stretching the ring using a tensile tester to about 100% extension for about 1 minute to identify a load; and
calculating the relaxed modulus using the formula:

Relaxed Modulus (MPa)=$(F \times d \times C)/2M$ wherein F is the load in Newtons, d is a density of the latex ring in grams per cubic centimeter, C is an external circumference of the dipping structure in centimeters, and M is the mass of the latex ring in grams.

10. The method of claim 1, further comprising drying the at least one layer of the prevulcanized compounded latex composition at a temperature in a range of about 80° C. to about 120° C. for a time of about 1 minute to about 10 minutes.

11. The method of claim 10, wherein the drying is carried out after the dipping and before the curing.

12. The method of claim 1, wherein the dipping comprises a first dipping effective to form a first layer of the prevulcanized compounded latex composition and a second effective to form a second layer of the prevulcanized compounded latex composition on the first layer of the prevulcanized compounded latex composition.

13. The method of claim 12, comprising a first drying that is carried out after the first dipping and before the second dipping and a second drying that is carried out after the second dipping.

14. The method of claim 13, wherein the first drying is carried out at a first temperature, the second drying is carried out at a second temperature, and the second temperature is higher than the first temperature.

15. The method of claim 13, wherein the first drying is carried out at a temperature in a range of about 80° C. to about 100° C. for a time of about 1 minute to about 10 minutes.

16. The method of claim 13, wherein the second drying is carried out at a temperature in a range of about 100° C. to about 120° C. for a time of about 1 minute to about 10 minutes.

* * * * *